United States Patent [19]

Epstein

[11] Patent Number: 4,576,175

[45] Date of Patent: Mar. 18, 1986

[54] BIOPSY ATTACHMENT FOR ULTRASONIC PROBE

[76] Inventor: Moshe Epstein, 1530 Beacon St., Brookline, Mass. 02146

[21] Appl. No.: 529,624

[22] Filed: Sep. 6, 1983

[51] Int. Cl.⁴ .............................................. A61B 10/00
[52] U.S. Cl. ..................................... 128/660; 408/72 B
[58] Field of Search .................... 128/660, 661, 24 A, 128/753, 754, 303.19, 329 R, 329 A, 305.1; 604/178; 408/72 R, 72 B

[56] References Cited

U.S. PATENT DOCUMENTS

| | | | |
|---|---|---|---|
| 3,017,887 | 1/1962 | Heyer | 604/178 X |
| 4,058,114 | 11/1977 | Soldver | 128/660 |
| 4,108,165 | 8/1978 | Kopp et al. | 128/660 |
| 4,151,834 | 5/1979 | Sato et al. | 128/660 |
| 4,249,539 | 2/1981 | Vilkomerson et al. | 128/660 |
| 4,289,139 | 9/1981 | Enjoji et al. | 128/660 |
| 4,346,717 | 8/1982 | Haerten | 128/660 |
| 4,363,326 | 12/1982 | Kopel | 128/660 |
| 4,402,324 | 9/1983 | Liudgren et al. | 128/660 |
| 4,497,325 | 2/1985 | Wedel | 128/754 |

Primary Examiner—Kyle L. Howell
Assistant Examiner—Francis J. Jaworski
Attorney, Agent, or Firm—Sandler & Greenblum

[57] ABSTRACT

A biopsy attachment for a probe having a transducer for producing a beam of ultrasonic energy includes a housing associated with the probe and a bushing having an axial aperture for receiving a biopsy needle. The housing has an aperture for attaching the bushing to the housing. The bushing and the housing are constructed and arranged so that by positioning the bushing in a first angular position relative to the housing, a lateral displacement of the bushing into the recess can take place until the bushing reaches an inserted position. Thereafter, rotation of the bushing in one direction from its first angular position to a second angular position causes the bushing to frictionally engage the housing retaining the bushing to the housing.

11 Claims, 10 Drawing Figures

BIOPSY ATTACHMENT FOR ULTRASONIC PROBE

TECHNICAL FIELD

This invention relates to a biopsy attachment for an ultrasonic probe used for medical purposes.

BACKGROUND OF THE INVENTION

Ultrasonic probes are widely used for medical diagnostic and treatment purposes. Recently, sector scan probes have become prominent. A typical sector scan probe is illustrated in U.S. Pat. No. 4,151,834, which shows a housing containing a DC servomotor that drives a mechanism for oscillating a transducer crystal. Periodically, the transducer pulsed with electrical signals causing an ultrasonic beam to be emitted periodically as the transducer oscillates between its angular limits. The rate at which the transducer is pulsed is many times greater than the rate of angular movement of the transducer; and for this reason, the beam is said to scan a sector. Tissue interfaces in the path of each beam reflect energy back to the transducer, and the electronic circuitry associated with the probe establishes the distance of the interface from the transducer in a conventional manner. Medically useful information is made available when the output of the probe is displayed on a cathode ray tube (CRT). That is to say, the CRT displays the sector swept out by the beam as the transducer oscillates, and the circuitry that responds to echoes modulates the image on the CRT for presenting a sectoral cross-section through a patient being imaged.

In order to correctly display images on the CRT, the angular position of the transducer must be accurately known; and, to this end, it is conventional to incorporate a position sensor into the probe for sensing the angular position of the transducer and to establish the azimuthal angle of the display in the CRT. The probe utilizes a servo-feedback circuit to control the position of the transducer, and the angular information thus determined is made available to the CRT for display purposes.

Some medical procedures are facilitated when a biopsy needle is used in conjunction with the ultrasonic probe, and for this reason special ultrasonic probes have been developed for this purpose. U.S. Pat. No. 4,108,165 is typical of conventional ultrasonic probes designed to facilitate the use of a biopsy needle. The U.S. Pat. No. 4,108,165 discloses an ultrasonic probe having an annular transducer periodically driven by an electronic circuit for producing ultrasonic beams that can be directed into the body of a patient under examination. No scanning of the beam is provided, however, and the transducer is mounted in a cylindrical housing having an axial bore concentric with the annular transducer. The housing contains a radial slit which extends the length of the housing, and which permits entry of a semi-circular tube attached to a stainless steel cap having a flange for receiving the opposite end of the housing opposite that contains the transducer.

The cap is also slotted so that after the cap and the tube are inserted into the probe, rotation of the cap will misalign the slot therein with the slotted housing, thereby defining a central circular opening into which a biopsy needle can be inserted for concentrically locating the biopsy needle within the probe. Spring loaded detents in the housing are engagable in a corresponding groove in the inner flange of the cap for the purpose of releasable holding the cap to the probe.

The arrangement in the U.S. Pat. No. 4,108,165 is suitable for many applications, but the complexity of the design, particularly the use of spring loaded detents and the complexity in manufacturing the stainless steel cap in terms of machining, result in a biopsy attachment which is complex and more expensive than necessary. In addition, the probe is not well adapted for use with a sector scan type of ultrasonic probe.

It is, therefore, an object of the present invention to provide a new and improved biopsy attachment for an ultrasonic probe which overcomes the above-described deficiencies in the prior art.

BRIEF DESCRIPTION OF THE INVENTION

According to the present invention, a biopsy attachment for a probe having a transducer for producing a beam of ultrasonic energy includes a housing associated with the probe and having a recess, a bushing having an axial aperture for receiving a biopsy needle, and cooperable means on the bushing and housing responsive to positioning the bushing in a first angular position receptive to the housing for effecting lateral displacement of the bushing into the recess to an inserted position, and responsive to rotation of the bushing in one direction, when in its inserted position, from its first angular position for frictionally holding the bushing in a second angular position.

In the preferred form of the invention, the recess in the housing is defined by a lug having a pair of spaced legs defining a key-hole shaped slot. The free ends of the legs define a relatively narrow portion of the slot, and the connected ends of the legs define a relatively enlarged portion. The bushing has one transverse dimension no larger than the relatively narrow portion of the slot, and the other transverse dimension of the body is no smaller than the relatively enlarged portion of the slot. As a consequence, the spaced legs of the lug are resiliently deflected by the body of the bushing when the latter is in its inserted position and is rotated from its first and to its second angular position. With this arrangement, the bushing is securely held in place by friction, yet can be inserted or removed easily merely by rotating the bushing relative to the legs.

To facilitate proper mounting of the bushing on the ultrasonic probe, a stop may be provided for limiting rotation of the bushing in one direction beyond its second angular position at which the bushing is frictionally captured by the legs. The stop may be a part of the body of the bushing containing the reduced and enlarged cross-section or a part of the head of the bushing.

Finally, the axis of the aperture in the bushing, when the latter is mounted in its operative position on the housing, is inclined with respect to the axis of the beam of the probe with the result that the needle, when inserted into the housing, lies within the scanned sector of the probe. In addition, the housing itself may be formed of a plastic material conforming to the shape of the probe, thereby making the biopsy attachment relatively inexpensive and disposable, facilitating its use for medical examination purposes.

BRIEF DESCRIPTION OF THE DRAWINGS

Embodiments of the invention are shown in the accompanying drawings, wherein.

DETAILED DESCRIPTION OF THE INVENTION

Figure 1:
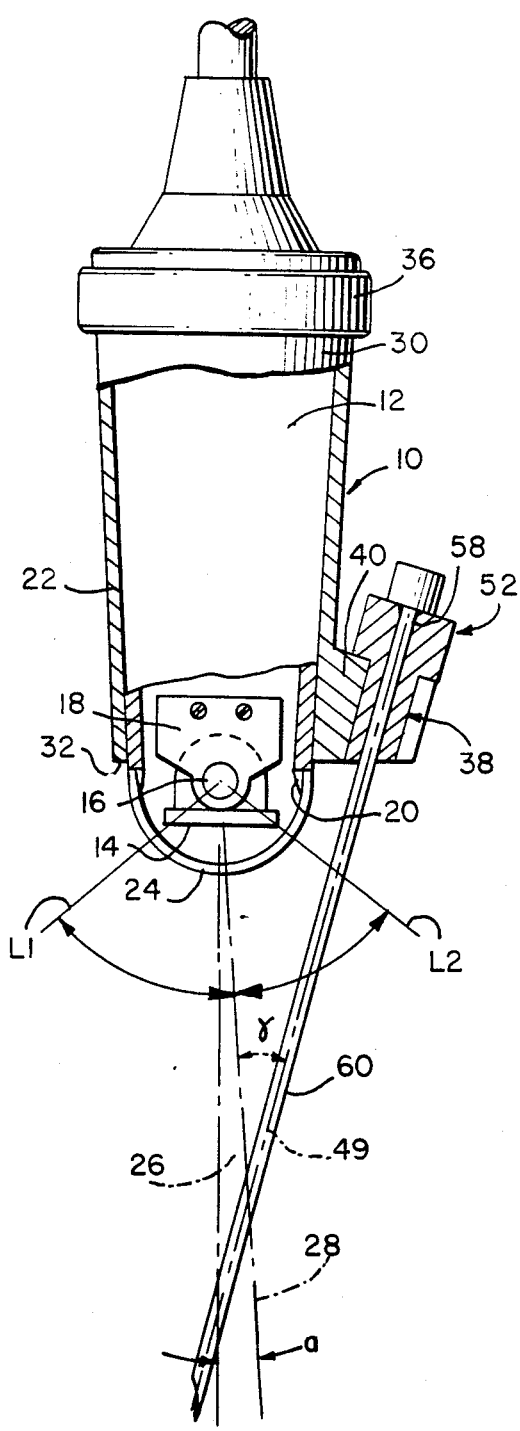
FIG. 1 is a vertical cross-section through an ultrasonic sector scanning probe to which the present invention is attached.

Referring now to FIG. 1, reference numeral 10 designates a biopsy attachment according to the present invention attached to sector scan ultrasonic probe 12. The details of probe 12 are of no concern in the present application, and only transducer 14 is shown in detail. Transducer 14 is mounted on pivot bearing 16 carried by mounting plates 18 rigidly attached to probe 12 adjacent open end 20 of casing 22 containing the probe. By a suitable mechanism (not shown), transducer 14 is oscillated between two limits designated L1 and L2 in FIG. 1.

Open end 20 of casing 22 is closed by a plastic sheath 24, which is transparent to sonic radiation produced by transducer 14 or reflected back to transducer 14 from an object producing an echo. Phantom line 26 defines the geometric center-line of the transducer; and the mechanism (not shown) housed within casing 22 causes the transducer to oscillate about axis 26 producing a beam whose azimuth angle changes from the angular position shown by line L1 to the angular position shown by line L2. This movement occurs at around 30-70 oscillations per second, while the transducer is pulsed at a rate many times faster than that. As a consequence, many beams are located within the limits defined by the lines L1, L2.

The actual center line of the beam designated by broken line 28 is displaced from the geometric center-line by the angle a. This angle is quite small and is an error whose magnitude depends on the precision with which the electronics driving the transducer and the transducer mounting itself are fashioned. As discussed previously, a sector scan probe has a DC motor that is servo controlled and a position sensor (not shown) which establishes the actual angle of the transducer and feeds this information back to the motor for controlling its operation. By suitable design, the angle a can be made very small.

Biopsy attachment 10 includes tubular housing 30 fashioned of relatively thin plastic material dimensioned to closely fit around probe 12, as shown in FIG. 1. The operational free end 32 of the housing is open permitting sheath 24 to project therethrough. The opposite axial end of housing 30 is also open and is threaded, as indicated at 34 in FIG. 2. Because sector-shaped probes are generally tapered, as indicated in FIG. 1, housing 30 is held in place with the probe by screw cap 36, which is releasably connected to the housing by screw threads 34. Thus, tightening of cap 36 draws housing 30 into close engagement with the probe.

Figure 2:
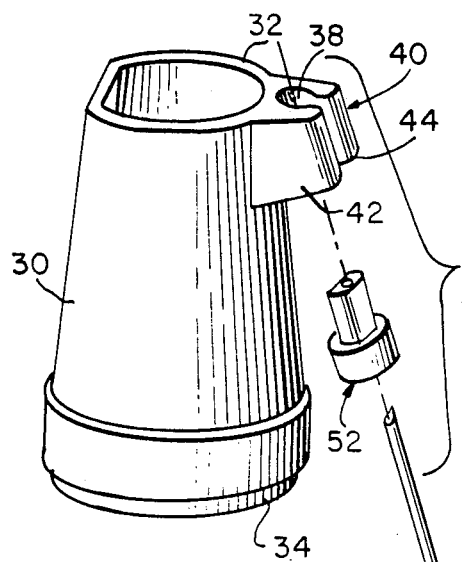
FIG. 2 is a perspective view of the biopsy attachment according to the present invention shown with its parts exploded.
Figure 5A:
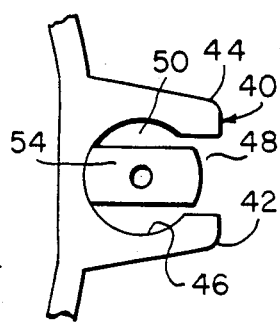
FIGS. 5A and 5B are fragmental views of the housing showing the bushing of the present invention inserted therein and in two different angular positions.
Figure 5B:
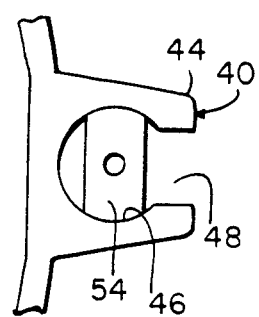

Adjacent free end 32 of the housing is recess 38 defined by lug 40 having a pair of spaced legs 42, 44. As shown in FIGS. 2 and 5b, for example, the spaced legs define a key-hole shaped slot 46. The free ends of the legs define a relatively narrow portion 48 of the slot, and the connected ends of the legs define a relatively enlarged portion 50 of the slot. As shown in FIG. 1, the axis of slot 48, designated by chainline 49, inclined relative to geometric axis 26 of the probe and, in fact, intersects the axis at some distance from the transducer.

Figure 3:
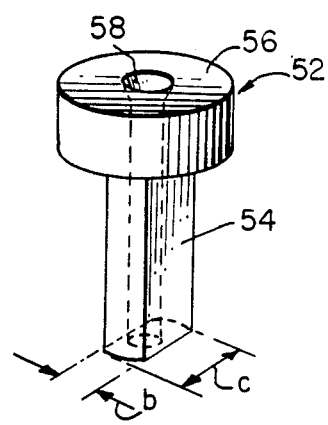
FIG. 3 is a perspective view of one form of the bushing according to the present invention.
Figure 4:
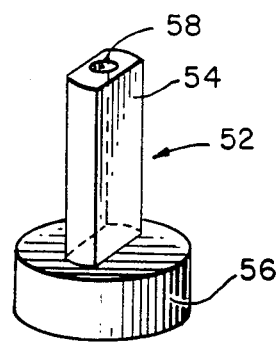
FIG. 4 is another view of the bushing shown in FIG. 3.

In addition to housing 30, the biopsy attachment of the present invention includes bushing 52, which preferably is of stainless steel. Bushing 52 comprises body 54 (see FIG. 3) having enlarged head 56 attached at one end. Axial aperture 58 passes through the bushing. The diameter of aperture 58 closely matches the diameter of biopsy needle 60 (FIGS. 1 and 2) and permits the biopsy needle to be slidably mated with the bushing.

Body 54 of the bushing has one transverse dimension b no larger than the relatively narrow portion 48 of slot 46. The other transverse dimension c of the body is made no smaller than the relatively enlarged portion 50 of the slot. In the embodiment shown in FIG. 3, head 56 of the bushing is circular and is made small enough in diameter to permit rotation of the bushing in slot 46.

In operation, biopsy needle 60 may be slidably inserted in axial aperture 58, and the resultant combination can be mounted on housing 30. In order to mount the combination, bushing 52 is oriented until its relatively small transverse dimension b is aligned with narrower portion 48 of slot 46, as shown in FIG. 5A. This is what termed herein the first angular position of the bushing relative to the housing; and, when the bushing is in this position, lateral displacement of the bushing into the recess can be effected until the bushing is located at its inserted position, as shown in FIG. 5A. Thereafter, the bushing may be rotated 90° in either direction from its first angular position into a second angular position at which the bushing frictionally engages to the housing thus securing the bushing to the housing.

The frictional engagement arises because dimension c is no less than, and preferably slightly more than, the dimension of enlarged opening 50 when the legs 42, 44 are unstressed. In this way, a biopsy needle can be attached quite easily, but securely, to the housing. Furthermore, the biopsy needle can be detached easily by following the opposite procedure used in attaching: namely, rotating the bushing from its second angular position to its first angular position and then laterally moving the bushing through the slot.

In order to securely hold the bushing to the housing and to prevent inadvertent rotation of the bushing to its first angular position at which the narrow dimension b is aligned with narrow opening 48, stops for limiting the angular rotation of the bushing in one direction can be provided. An arrangement for this is shown in FIGS. 6A and 6B, to which reference is now made.

Figure 6A:
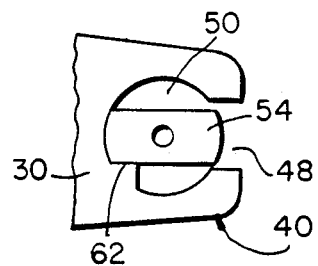
FIGS. 6A and 6B are views similar to FIGS. 5A and 5B, but showing one form of stop means for limiting angular rotation of the bushing relative to the housing.
Figure 6B:
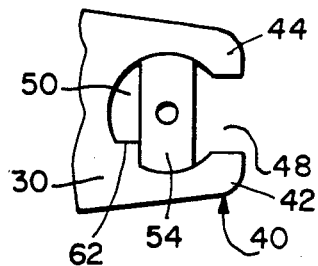

As shown in FIGS. 6A and 6B, stop 62 is provided as part of the lugs, the stop being eccentrically located with respect to the axis of the aperture in the lug.

In operation, the bushing is oriented in its first angular position so that the smaller dimension b is aligned with the narrower opening 48, allowing the bushing to enter into the slot, as shown in FIG. 6A. Lateral insertion of the bushing is halted when the body of the bushing reaches the innermost part of enlarged portion 50, as shown in FIG. 6A. Thereafter, the bushing may be rotated in one direction, and one direction only (clockwise, as seen in FIG. 6B) until the wider dimension c engages stop 62. Further rotation of the bushing in this direction is precluded, and the larger transverse dimension frictionally engages legs 42, 44 for holding the bushing to the housing.

Figure 7:
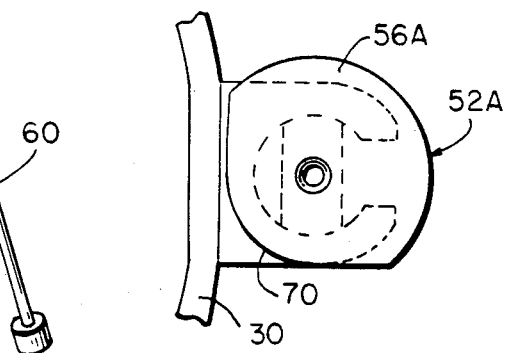
FIG. 7 is a view similar to FIG. 6B, but showing a different form of stop means for limiting angular rotation of the bushing.
Figure 8:
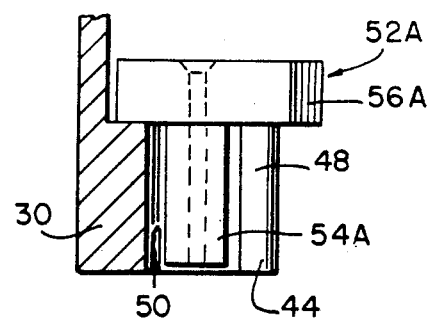
FIG. 8 is a side view of the bushing shown in FIG. 7.

An alternative stop arrangement is illustrated in FIGS. 7 and 8. In this embodiment, the head of the bushing is not symmetrical with respect to the axis of the bushing. Specifically, bushing 52A includes body 54A, enlarged head 56A, which is eccentric with respect to the axis of the bushing (FIG. 7). Reduced portion 70 of head 56A permits the bushing to be inserted into slot 46 in the housing when the smaller transverse dimension of the body is aligned with opening 48. After insertion occurs, the bushing may be rotated to the position shown in FIG. 7 where the reduced portion 70 abuts housing 30 for the purpose of limiting further rotation.

The arrangement described above is relatively simple in configuration and is thus easily and inexpensively manufactured. Furthermore, the components of the biopsy attachment according to the present invention have no moving parts and, as a consequence, can be sterilized easily and sealed for future use without being concerned about parts that must move relative to each other in assembly and use.

It is believed that the advantages and improved results furnished by the method and apparatus of the present invention are apparent from the foregoing description of the preferred embodiment of the invention. Various changes and modifications may be made without departing from the spirit and scope of the invention as described in the claims that follow.

I claim:

1. A biopsy attachment for a probe having a transducer for producing a beam of ultrasonic energy, said attachment comprising:
   (a) a housing associated with the probe and having a recess;
   (b) a bushing having an axial aperture of given length for receiving a biopsy needle and surrounding, engaging and supporting said needle throughout said length; and
   (c) said bushing and said housing having cooperable means responsive to positioning the bushing in a first angular position relative to the housing for effecting displacement of the bushing into the recess to an inserted position, and responsive to the rotation of the bushing in one direction, when in its inserted position, from its first angular position, for frictionally holding the bushing in a second angular position.

2. A biopsy attachment according to claim 1 wherein said cooperable means includes a stop for limiting rotation of the bushing in said one direction beyond said second angular position.

3. A biopsy attachment according to claim 1 wherein the axis of the aperture in the bushing intersects the axis of the beam when the bushing is in its inserted position.

4. A biopsy attachment according to claim 1 wherein the recess in the housing in the form of a lug having a pair of spaced legs defining a key-hole shaped slot, the free ends of the legs defining a relatively narrow portion of the slot, and the connected ends of the legs defining a relatively enlarged portion of the slot, said cooperable means comprising a body on the bushing having one first transverse dimension no larger than the relatively narrow portion of the slot, the other transverse dimension of the body being no smaller than the relatively enlarged portion of the body.

5. A biopsy attachment according to claim 4 wherein the spaced legs are resiliently deflected by the body of the bushing when the latter is in its inserted position and is rotated from said first to said second angular position.

6. A biopsy attachment according to claim 5, including stop means for limiting rotation of the bushing in one direction beyond said second angular position.

7. A biopsy attachment according to claim 6 wherein said stop means interacts with the body of the bushing.

8. A biopsy attachment according to claim 4 wherein the bushing has a head defining a flange that overlies the lug for limiting axial displacement in one direction of the bushing relative to the housing.

9. A biopsy attachment according to claim 8 wherein said stop means interacts with the head of the bushing.

10. An ultrasonic probe in combination with the biopsy attachment of claim 9 and a biopsy needle for insertion into the aperture within the bushing, the transducer producing an oscillating ultrasonic beam defining a sector that includes the needle when the latter is inserted into the aperture in the bushing.

11. The combination of claim 10 wherein the housing is separate from and releasably attached to the probe.

* * * * *